United States Patent [19]

Sjostrom

[11] Patent Number: 5,024,659
[45] Date of Patent: Jun. 18, 1991

[54] BREAKABLE NEEDLE AND HINGED NEEDLE GUIDE

[75] Inventor: Douglas D. Sjostrom, Wakefield, Mass.

[73] Assignee: Smith & Nephew Dyonics Inc., Andover, Mass.

[21] Appl. No.: 463,176

[22] Filed: Jan. 10, 1990

[51] Int. Cl.⁵ .............................................. A61M 5/50
[52] U.S. Cl. .................................... 604/110; 604/164; 604/198; 604/272
[58] Field of Search ........................ 604/110, 164–166, 604/272, 198

[56] References Cited

U.S. PATENT DOCUMENTS

| | | | |
|---|---|---|---|
| 2,899,960 | 8/1959 | Ginsburg | 604/272 X |
| 3,470,604 | 10/1969 | Zenick | 604/272 X |
| 3,712,302 | 1/1973 | Burke et al. | 604/110 |
| 3,993,079 | 11/1976 | Henriques de Gatztanondo | 604/272 X |
| 4,007,740 | 2/1977 | Owen | 604/192 |
| 4,220,151 | 9/1980 | Whitney | 604/110 |
| 4,545,374 | 10/1985 | Jacobson | 604/164 X |
| 4,573,448 | 3/1986 | Kambin . | |
| 4,609,370 | 9/1986 | Morrison | 604/165 |
| 4,627,838 | 12/1986 | Cross et al. | 604/105 |
| 4,846,804 | 7/1989 | Davis et al. | 604/164 |
| 4,878,904 | 11/1989 | Callaway | 604/273 |

OTHER PUBLICATIONS

J. A. N. Shepperd et al., "Percutaneous Disc Surgery", 238 Clinical Orthopaedics and Related Research 43 (Jan. 1989).

*Primary Examiner*—John D. Yasko
*Assistant Examiner*—Adam J. Cermak
*Attorney, Agent, or Firm*—Kirkpatrick & Lockhart

[57] ABSTRACT

A needle guide is provided which includes a hub and a needle connected to the hub. A stylet may also be provided for insertion into the hollow interior of the needle to aid in the insertion of the needle through tissue. The needle has a transverse breaking section, preferably a groove, adjacent to the hub. The breaking section is configured so that the needle will break cleanly in two at the breaking section when the hub is bent back and forth relative to the portion of the needle distal to the breaking section. An alternative embodiment of the needle guide provides a handle which extends from the hub over the needle. A hinge is provided in alignment with the needle breaking section to permit the handle to be flexed relative to the hub when the hub is moved back and forth in the manner described.

6 Claims, 2 Drawing Sheets

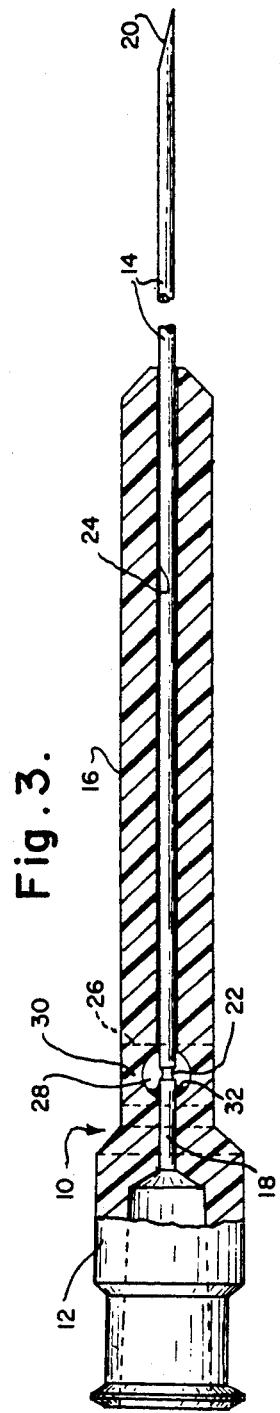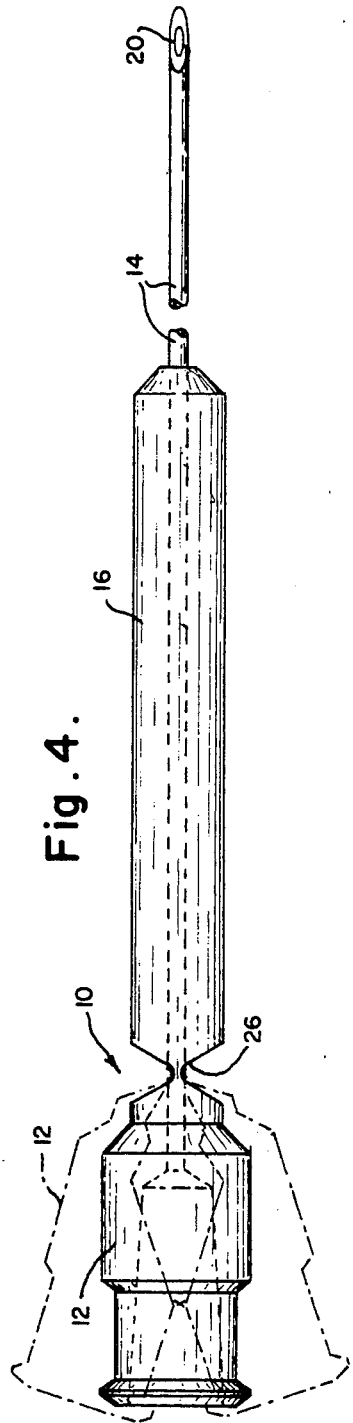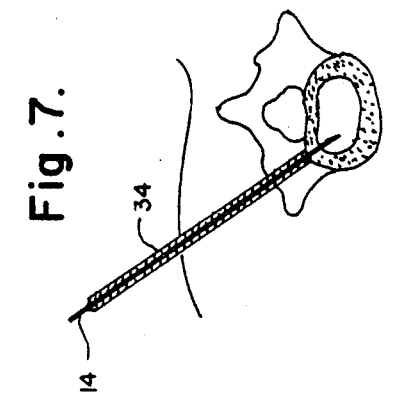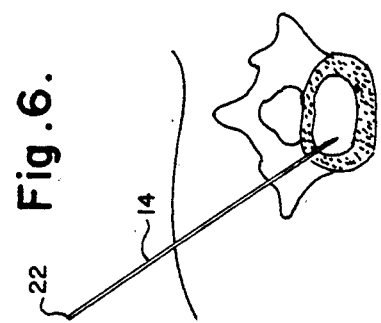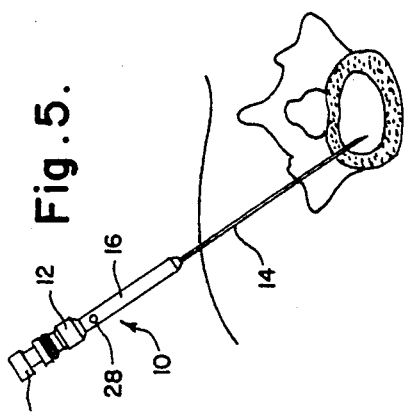

BREAKABLE NEEDLE AND HINGED NEEDLE GUIDE

BACKGROUND OF THE INVENTION

1. Field of the Invention

The present invention relates to needle guides for use in surgery and more particularly, to a needle guide that can be detached during surgery from its hub.

2. Description of the Prior Art

In the performance of minimally invasive percutaneous surgical procedures, it is necessary to establish the surgical portal with minimal trauma using a spinal needle or similar device. Such procedures may include those performed on deep joints, such as the hip or spine, cardiovascular procedures, such as balloon angioplasty, or any application requiring accurate atraumatic placement of the surgical portal, with subsequent enlargement for the introduction of larger operative instrumentation.

In percutaneous disc surgery, for example, a hypodermic needle is often used in order to confirm proper placement in a deep joint by injecting a radiopaque dye for discography. Typically, a sharp spinal needle is directed toward the intervertebral disc under flouroscopic control and is followed by insertion of successive tubes, or cannulas, of increasing diameter.

Kambin U.S. Pat. No. 4,573,448 describes a method for decompressing herniated intervertebral discs which includes the steps of inserting a hollow needle with a stylet through the patient's skin at a desired location, removing the stylet, introducing a guide wire through the needle, withdrawing the needle while keeping the guide wire in place and subsequently passing a trocar over the guide wire. The guide wire is then removed and a cannula is passed over the trocar. The trocar is removed and a cutting instrument is introduced through the cannula.

An article by J. A. N. Shepperd et al., "Percutaneous Disc Surgery" 238 Clinical Orthopaedics and Related Research 43 (Jan. 1989), describes the use of a discogram needle with a detachable hub which is used in place of a separate guide wire. The discogram needle and probing cannula are inserted into the disc. The needle is retained there as an anchor. The article states that the needle hub is removed to permit withdrawal of the probing cannula, leaving the needle to act as a guide wire. There is, however, no description or suggestion of the means of removing the hub from the needle.

Another known procedure for percutaneous nucleotomy employs a discography needle which fits within an external sheath. The needle is inserted into the intervertebral disc. Following completion of the discography, the needle is withdrawn leaving the sheath in place. Cannulas are then introduced over the external sheath.

There is some risk associated with the insertion of the tubes, or cannulas over a guide wire. If the guide wire is inadvertently moved during the withdrawal of the needle, the subsequent insertion of the cannulas over the guide wire will be imprecise. An object of the present invention is to reduce the risk of inadvertently moving the guide wire when removing the needle. A further object is to provide a needle guide which can be adapted to function as a guide wire for the subsequent insertion of a cannula without removal of the needle once accurately placed. Another object of the present invention is to provide such a needle guide which is simply constructed and simple to use.

SUMMARY OF THE INVENTION

The present invention provides a needle guide which includes a hub and a needle aligned coaxially with the hub and having a proximal end connected to the hub and a distal end. The needle also includes a transverse breaking section adjacent to the hub. The breaking section is configured so that the needle breaks in two at the breaking section when a transverse bending force is applied to the hub. The force is preferably applied by bending the hub back and forth relative to the portion of the needle distal to the breaking section. The needle is preferably hollow. The breaking section is preferably a groove formed in the needle.

The needle guide may also include a hollow handle extending distally from the hub over and concentric to the needle for a distance distal to the breaking section. The handle includes a hinge means adjacent to the hub in alignment with the breaking section so that the handle flexes relative to the hub at the hinge means when the transverse force is applied. The hinge means preferably includes an open area immediately surrounding the breaking section of the needle and a flexible area connecting the handle to the hub.

BRIEF DESCRIPTION OF THE DRAWINGS

The present invention will be better understood by reference to the drawings in which:

FIG. 3 is a section view of an alternative embodiment of the needle guide of the present invention;

FIG. 4 is a view of the needle guide of FIG. 3 showing the hub being bent back and forth to flex the handle and break the needle;

FIG. 5 is a view of the needle guide of FIG. 3 with the stylet of FIG. 8 inserted into the operative portal for percutaneous lateral discectomy;

FIG. 6 is a view of the inserted needle guide of FIG. 5 following detachment and removal of the hub and the handle;

FIG. 7 is a view of the needle guide of FIG. 6 serving as a guide means for the introduction of a larger cannulated obturator.

DETAILED DESCRIPTION OF THE PREFERRED EMBODIMENTS

Figure 1:
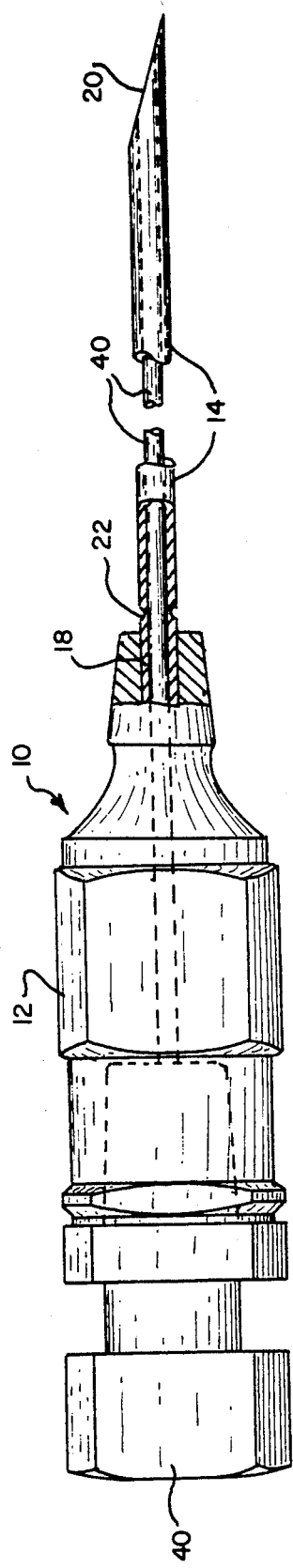
FIG. 1 is a partial section view of a preferred embodiment of the needle guide of the present invention with a stylet inserted through the needle guide.

FIGS. 1 through 4 illustrate the preferred embodiments of the needle guide 10 of the present invention. The needle guide 10 includes generally a hub 12 and a tubular needle 14. In the alternative embodiment shown in FIGS. 3 and 4, a handle 16 is also provided. Needle 14 is preferably made from type 304 seamless drawn tubing and is swage assembled into a metal luer taper hub 12. The needle 14 includes a proximal end 18 and a distal end 20. A beveled section at distal end 20 forms the needle's point. The needle 14 is preferably hollow. There is a breaking section, preferably a groove 22, adjacent to the hub 12 at the proximal end 18 of the needle 14. The breaking section, or groove 22 is transverse to the longitudinal axis of the needle 14. The proportions of groove 22 are determined by the specific size of needle 14. An 18 guage needle, for example, having a 0.050" outer diameter and a 0.0085" wall, would preferably have a groove 22 which is approximately one and one half the wall thickness in width and one half the wall thickness in depth.

Figure 2:
FIG. 2 is a partial section view of the needle of FIG. 1 after it has been broken away from the hub.

When the user grasps the needle shank distal to groove 22 and bends hub 12 back and forth relative to that portion of needle 14 distal to groove 22, as shown in FIG. 4, a transverse force is applied to hub 12 causing the needle 14 to break into two pieces at groove 22 to permit the hub 12 to be detached from needle 14. FIG. 2 illustrates the needle 14 after the hub 12 has been detached from the needle 14 at groove 22. The groove 22 is dimensioned to break cleanly and easily. When hub 12 is bent back and forth as described, the needle shank is then free to assume the role of a guide wire.

FIGS. 3 and 4 illustrate an alternative embodiment of the needle guide 10. A handle 16 is flexibly connected to hub 12. The handle 16 extends distally from the hub 16 over a distance along the length of needle 14. Handle 16 is concentric to needle 14. Handle 16 has a central bore 24 through which needle 14 passes. The end of needle 14 proximal to groove 22 is bonded or insert molded into the hub/handle as shown in FIG. 3 at 32. Bore 24 is dimensioned to permit handle 16 to slide easily over that portion of needle 14 distal to groove 22. Referring to FIG. 3, handle 16 includes a transverse hinge means 26 adjacent to hub 16 in alignment with groove 22. Hinge means 26 includes an open area 28 immediately surrounding groove 22 to expose groove 22 to viewing and a flexible section 30 connecting handle 16 to hub 12. When a transverse force is applied, for example, by bending hub 12 is bent back and forth relative to handle 16 as shown in FIG. 4, the handle 16 flexes relative to hub 12 at hinge means 26. At the same time, needle 14 breaks into two at groove 22. The hub 12 and handle 16 can then slide easily off of needle 14.

Figure 8:
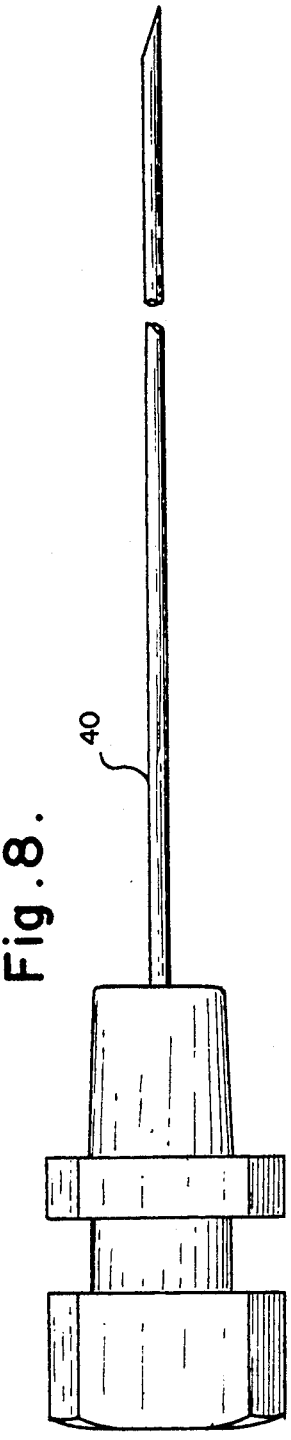
FIG. 8 is a view of a stylet for insertion through the hollow interior of the needle of FIGS. 1 or 3.

The hub 12 and handle 16 can be made of plastic. The extended handle 16 provides increased rigidity when it is necessary to use a long needle 14 to achieve the desired guide function. A stylet 40, as shown in FIG. 8, may also be provided for insertion through the hollow interior of the needle 14. The stylet provides rigidity to the needle 14 which is beneficial when inserting the needle into the spine. It should be dimensioned to fill the hollow interior of at least the tip of the needle 14 so that the needle can pass through tissue cleanly.

FIGS. 5 through 7 illustrate the needle guide 10 of the present invention in use. FIG. 5 shows the typical placement of the operative portal for percutaneous lateral discectomy. When inserted, stylet 40 is in place. Following insertion, the stylet is removed. The needle remains in position. At this point the surgeon may perform discography by attaching a syringe and injecting radiopaque media into the vertebral disc. When there is no further need for the needle guide 10 to function as a hypodermic needle, the user grasps handle 16 with one hand and hub 12 with the other and bends hub 12 back and forth perpendicular to the plane of hinge means 26 at flexible section 30 to achieve a clean break of needle 14 at groove 22, visible through open area 28. The hub 12 and handle 16 are then removed. The needle 14 remains, as shown in FIG. 6, to function as a guide wire for the subsequent introduction of a larger cannulated obturator 34, as shown in FIG. 7. Thereafter the needle 14 is withdrawn through cannula 34, and another cannula is passed over cannula 34 until its distal end reaches the annulus fibrosis of the disc. Cannula 34 is then withdrawn. A cutting instrument may then be introduced through the cannula to permit the surgeon to work on the disc.

The needle guide 10 of the present invention eliminates the step of inserting a guide wire through the hypodermic needle and withdrawing the needle. The needle 14 is free to function as the guide wire due to the means provided for detaching the hub 2 from the needle 14.

What is claimed is:

1. A needle guide comprising:
   a hub having a longitudinal axis;
   a needle having a longitudinal axis aligned coaxially with said longitudinal axis of said hub and having a proximal end connected to said hub and a distal end;
   said needle having a transverse breaking section adjacent said hub, said breaking section being configured so that said needle breaks in two at said breaking section when a transverse breaking force is applied to said hub; and
   a hollow handle extending distally from said hub over and concentric to said needle for a distance distal to said breaking section, said handle having a transverse hinge means adjacent said hub in alignment with said breaking section so that said handle flexes relative to said hub at said hinge means when said transverse force is applied.

2. The needle guide recited in claim 1 wherein said needle is hollow.

3. The needle guide recited in claim 2 further comprising a stylet for insertion into the hollow interior of said needle.

4. The needle guide recited in claim 1 wherein said hinge means has an open area immediately surrounding said breaking section and a flexible area connecting said handle to said hub.

5. The needle guide recited in claim 1 wherein said breaking section is a groove formed in said needle.

6. A method of using a needle guide having a hub and handle, in surgery on a patient comprising:
   inserting a needle guide having a hub and a needle distal thereto into a patient at a desired location;
   applying a transverse breaking force at a transverse breaking section on the needle proximate the hub to break the needle at said breaking section;
   removing the hub and the portion of the needle broken away;
   guiding a cannulated instrument over the portion of the needle remaining in the patient to the desired location; and
   removing the needle through the cannulated instrument.

* * * * *

UNITED STATES PATENT AND TRADEMARK OFFICE
CERTIFICATE OF CORRECTION

PATENT NO. : 5,024,659
DATED : June 18, 1991
INVENTOR(S) : Douglas D. Sjostrom

It is certified that error appears in the above-identified patent and that said Letters Patent is hereby corrected as shown below:

Col. 4, line 15, delete "2" and substitute --12-- therefor.

Signed and Sealed this

Fifteenth Day of December, 1992

Attest:

DOUGLAS B. COMER

*Attesting Officer*      Acting Commissioner of Patents and Trademarks